United States Patent [19]

Erwin

[11] Patent Number: 5,575,996
[45] Date of Patent: Nov. 19, 1996

[54] INSECTICIDE BAIT COMPOSITION

[76] Inventor: Barry C. Erwin, 707 Park Ave., Monroe, La. 71201

[21] Appl. No.: 533,264

[22] Filed: Sep. 25, 1995

Related U.S. Application Data

[62] Division of Ser. No. 201,892, Feb. 25, 1994, Pat. No. 5,480,638.

[51] Int. Cl.$^6$ .......................... A01N 25/12; A01N 59/14; A01N 65/00
[52] U.S. Cl. ................... 424/84; 424/659; 514/65
[58] Field of Search ................ 424/84, 659; 514/65

[56] References Cited

U.S. PATENT DOCUMENTS

| | | | |
|---|---|---|---|
| 3,691,239 | 9/1972 | Hackett et al. | 260/652 P |
| 3,962,458 | 6/1976 | Schrider | 424/304 |
| 4,049,460 | 9/1977 | Broadbent | 106/15 R |
| 4,438,090 | 3/1984 | Brite | 424/7.1 |
| 4,461,758 | 7/1984 | Brite | 424/10 |
| 4,464,443 | 8/1984 | Farrell et al. | 428/688 |
| 4,514,960 | 5/1985 | Sears | 53/440 |
| 4,759,930 | 7/1988 | Granirer et al. | 424/148 |
| 5,047,424 | 9/1991 | Puritch et al. | 514/521 |
| 5,066,482 | 11/1991 | Kohn et al. | 424/45 |

Primary Examiner—Peter O'Sullivan
Attorney, Agent, or Firm—John M. Harrison

[57] ABSTRACT

A powdered insecticide bait composition which includes powdered dry pet food, powdered pyrethrin or pyrethroid and boric acid killing ingredients and a powdered clay drying agent. A method for preparing the composition, including the steps of grinding the dry pet food into a powder, adding the powdered pyrethrin and boric acid killing ingredients to the pet food granules and thoroughly mixing the ingredients. The resulting powdered mixture can be sprinkled around the baseboards of a structure to kill roaches or other scavenging insects and on ant mounds to kill ants, including fire ants. An additional step in preparing the composition includes a powdered oil-soak type clay drying agent to the mixture to maintain the mixture in a dry, fine, flowable powder.

8 Claims, No Drawings

INSECTICIDE BAIT COMPOSITION

This is a divisional of application Ser. No. 08/201,892, filed on Feb. 25, 1994, now U.S. Pat. No. 5,480,638.

BACKGROUND OF THE INVENTION

1. Field of the Invention

This invention relates to insecticidal compositions effective for killing insects and more particularly, to an environmentally safe powdered insecticide bait composition for luring and killing a variety of scavenging pest insects and a method for preparing the composition. In a preferred embodiment of the invention, a commercially-prepared, dry pet food such as dog food is initially milled, ground or otherwise comminuted to a particle size between a 100 mesh and 400 mesh screen size. A pet food having a high fat content is preferred, since food of this character is more effective in attracting both German and American cockroaches, fire ants and other scavenging insects, than is food having a low fat content. Powdered boric acid having a particle size smaller than a 250 mesh screen is then blended with the pet food. Boric acid is used because it has a proven long-lasting residual cockroach-killing capability and is non-toxic to mammals in the indicated concentrations, including livestock and domestic animals such as cattle, sheep, horses, dogs, cats, as well as zoo and laboratory animals and the like, A powdered pyrethrin or pyrethroid killing ingredient, preferably a synthetic pyrethrin devoid of solvents, is next blended with the boric acid mixture, Synthetic pyrethrins exhibit very effective insect control, have little odor and, like boric acid, are non-toxic to mammals in the indicated concentrations, An absorbent clay drying agent having a particle size smaller than 250 mesh, is preferably blended with the mixture in sufficient quantity to insure flowability of the powdered mixture. The drying agent removes moisture from the pet food particles, preventing the mixture from clumping and thus enabling it to be freely flowable and easily dispensed from a container. The resulting non-toxic and easy-to-use, powdered mixture has been found to be very effective in attracting and eliminating not only American and German cockroaches, but also ants, scavenging beatles, crickets, earwigs, houseflies, termites and virtually any other type of scavenging insect.

2. Description of the Prior Art

Several compounds are known in the art for eliminating ants, cockroaches and other undesirable insects. U.S. Pat. No. 3,962,458, dated Jun. 8, 1976, to Michael S. Schrider, details a "Systemic Control of Ectoparasites With Pyrethroids", utilizing m-phenoxybenzyl esters of spirocarboxylic acids as systemic insecticidal and acaricidal agents for treatment of homothermic animals. U.S. Pat. No. 4,438,090, dated Mar. 20, 1984, to Alan D. Brite, discloses a "Method of Preparing an Insecticide Containing Boric Acid", including the steps of milling the boric acid to a desired particle size, blending the boric acid particles with magnesium stearate, silica gel or tricalcium phosphate, adding sucrose octa-acetate or denatonium benzoate, adding a non-white powdered pigment, and electrically charging the particles of the resulting insecticide mixture. U.S. Pat. No. 4,461,758, dated Jul. 24, 1984, also to Alan D. Brite, describes an "Insecticide Including Powdered Boric Acid", characterized by a mixture of powdered boric acid, sucrose octa-acetate or denatonium benzoate, magnesium stearate, silica gel or tricalcium phosphate, and a nonwhite powdered pigment. U.S. Pat. No. 4,759,930, dated Jul. 26, 1988, to Marc S. Granirer, et al, details "Insect Killing Compositions and Method of Killing Insects Employing a Synergistic Mixture of Pyrethrum, Eucalyptus, Rosemary and Peppermint". The compositions are characterized by a powder, including a mixture of pyrethrum and/or rotenone and one or more of the following: eucalyptus, rosemary, peppermint and boric acid. U.S. Pat. No. 5,047,424, dated Sep. 10, 1991, to George S. Puritch, et al, discloses an "Environmentally Safe Insecticide", including a mixture of monocarboxylic acids and their alkali metal salts and a pyrethroid compound.

An object of this invention is to provide an insecticide bait composition of low toxicity and extremely low application rate, for effectively killing a variety of undesirable insects.

Another object of this invention is to provide a powdered insecticide bait composition of minimum active ingredient, combined with extremely low application rate, which is substantially nontoxic, odorless, requires no solvents or other ingredients and includes commercial pet food, boric acid and a pyrethrin or pyrethroid killing ingredient.

Yet another object of this invention is to provide an environmentally safe, ready-to-use insecticide bait composition characterized by a fine, dry, readily-flowable powder which is easily dispensed from a selected container and includes commercial pet food, boric acid, a pyrethrin or pyrethroid and a clay drying agent.

An even further object of this invention is to provide a method for preparing an insecticide bait composition, including the steps of grinding, pulverizing or comminuting dry, commercial pet food into a flowable powder, mixing powdered boric acid with the pet food and blending a powdered pyrethrin or pyrethroid ingredient with the pet food and boric acid mixture.

Still another object of this invention is to provide a method for preparing a powdered insecticide bait composition, which includes the steps of milling or grinding and screening dry, commercial pet food, mixing a powdered synthetic pyrethrin or pyrethroid and powdered boric acid with the ground pet food as killing ingredients and adding a clay drying agent to the mixture to maintain the mixture in a dry, finely powdered, readily flowable state.

SUMMARY OF THE INVENTION

These and other objects of the invention are provided in a powdered, odorless, substantially non-toxic, easily-dispensed and effective, environmentally-safe insecticide bait composition characterized by a powdered pet food having a high fat content, powdered pyrethrin and boric acid killing ingredients and a powdered clay-base drying agent, all blended as a flowable powder. A method of preparing the powdered bait composition includes the steps of grinding, milling or otherwise comminuting dry, commercial pet food, screening the pet food particles, mixing a powdered synthetic pyrethrin or pyrethroid and powdered boric acid with the powdered pet food as killing agents and adding a powdered clay drying agent to the mixture to mechanically disperse the powdered ingredients, dry the water from the pet food ingredient, coat the greasy pet food particles and maintain the mixture in a dry, fine, flowable powder state.

DESCRIPTION OF THE PREFERRED EMBODIMENTS

In a preferred embodiment of the invention, dry, commercial pet food such as dog food is initially ground or comminuted in a grinder such as a grist mill or coffee grinder and forced through the mesh of a screen such as a window screen to form small granules which have a particle size between about 100 mesh and about 400 mesh and are collected in a container. Because food having a high fat content tends to attract cockroaches, ants and other scavenging insects more effectively than does food having little or no fat, the dog food utilized in this invention preferably has a fat content equal to or greater than about 12 percent by weight. Typical of pet foods which may be used in the invention is "Dog Chow" (trademark) manufactured by the Purina Company of St. Louis, Mo. "Dog Chow" exists as chunks characterized by a mixture of ground yellow corn, soybean meal, meat and bone meal, ground meat and animal fat, in addition to other ingredients. Dry, powdered, commercial-grade boric acid may be then screened, if necessary, to form particles smaller than 250 mesh and is collected in the container. The powdered boric acid is thoroughly mixed with the dog food granules and dry, powdered, synthetic pyrethrin may likewise be screened and collected in the container. The powdered form of the pyrethrin is used because it includes no solvents, which may repel certain cockroaches and other scavenging insects. The pyrethrin is then thoroughly mixed with the dog food and boric acid mixture. After mixing, the powdered pyrethrin and boric acid particles adhere to the pet food particles due to the oil and moisture remaining in the dog food particles. An oil-soak type, pelletized clay drying agent such as "Floor-Guard" (trademark) manufactured for Specialty Oil Company of Shreveport, La., may be comminuted to a particle size smaller than about 250 mesh and thoroughly mixed with the powdered mixture in the container. Alternatively, powdered clay drying agents may be used to eliminate the size-reduction step. The clay drying agent is a multi-purpose colloidal absorbent and is capable of coating the pet food particles and absorbing most of the moisture in the pet food particles, maintaining the mixture in a fine, dry, powdered and easily-flowable state, which is easily dispensed from a container of selected design into cracks and crevices and on ant beds.

It is understood that the insecticide bait composition of this invention may be prepared using the ingredients described above, but without the addition of the clay drying agent to the powdered dog food, boric acid and pyrethrin mixture. However, the drying agent is preferably added to the mixture for the purpose of coating the oily pet food particles and removing excess moisture from the pet food particles to prevent clumping of the mixture, and thus enables the composition to be emptied from the dispensing container as an easily flowing powder and applied to small cracks and crevices more easily. The clay-base drying agent does not convey any appreciable insecticidal properties on the insecticidal bait composition or contribute to the non-toxic or odorless characteristics of the composition.

The invention will be better understood by reference to the following examples:

EXAMPLE 1

Six pounds of Purina Dog Chow dog food was ground in a coffee grinder and passed through a screen to form granules having a size between 100 mesh and 400 mesh and the screened granules were collected in a container. One pound of powdered commercial-grade boric acid was then sifted through a screen to form particles having a size smaller than 250 mesh and the boric acid particles were collected in the container. The dog food granules were then thoroughly mixed with the boric acid particles. 1.33 ounces of powdered, dry, commercial-grade, 40% pure synthetic pyrethrin was then screened, collected in the container and then thoroughly blended with the powdered mixture in the container. One pound of "Floor-Guard" absorbent was ground and passed through the screen to form particles having a size smaller than 250 mesh and the particles were added to the container and thoroughly blended with the mixture. The resulting fine powdered mixture was removed from the mixing container and packaged in dispensing containers of a selected size and shape.

EXAMPLE 2

Six pounds of Purina Dog Chow dog food was ground in a coffee grinder and passed through a 100 mesh screen and the granules were collected in a container. One pound of commercial-grade powdered boric acid was then added to the container and the dog food granules were thoroughly mixed with the boric acid particles. 1.33 ounces of powdered, dry, commercial-grade, 40% pure synthetic pyrethrin was then added to the container and the mixture thoroughly mechanically blended. The resulting mixture was removed from the mixing container and packaged in dispensing containers of a selected size and shape.

It will be appreciated that substantially any pyrethrin or pyrethroid compound having insecticidal activity is useful in the practice of this invention, including the pyrethroids inumerated in U.S. Pat. No. 5,047,424 to Purtich, et al at column 4, lines 45–55. The pyrethroids identified in U.S. Pat. No. 3,962,458 to Schnider are also appropriate insect killing agents for use in the compound of this invention. The concentration of pyrethrin used in the insecticide bait composition of this invention compares favorably with the concentrations inumerated in these patents. Pyrethrin for use as a killing agent of the composition may be extracted as a powder from the seeds, flowers or leaves of the composite family, of the genus chrysanthemum. However, a most preferred ingredient is synthetic pyrethrin or pyrethroid which are well known to those skilled in the art.

While the preferred embodiments of the invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A method of preparing an environmentally safe insecticide composition comprising a comminuted, flowable mixture of dry pet food comprising by weight at least from about 8% to about 12% fat, a colloidal drying agent for coating and absorbing moisture from said pet food, powdered boric acid present in said composition in a weight percent of from about 10% to about 18% and a synthetic pyrethrin present in said composition in a weight percent of from about 0.25% to about 0.55%, comprising the steps of comminuting dry pet food, mixing the pet food with powdered boric acid and a powdered pyrethrin in an effective insecticidal amount of said boric acid and said pyrethrin, to form a flowable powdered mixture and mixing a comminuted drying agent with said powdered mixture to coat said pet food and absorb excess moisture from said pet food.

2. The method of claim 1 comprising the step of comminuting said pet food to a particle screen size of between about 100 mesh and about 400 mesh prior to mixing said pet food with said boric acid and said pyrethrin.

3. The method of claim 1 comprising the step of screening said boric acid to a particle screen size smaller than about 250 mesh prior to mixing said boric acid with said pet food and said pyrethrin.

4. The method of claim 1 comprising the steps of:
   (a) screening said boric acid to a particle screen size smaller than about 250 mesh prior to mixing said boric acid with said pet food and said pyrethrin; and
   (b) comminuting said pet food to a particle screen size between about 100 mesh and about 400 mesh prior to mixing said pet food with said boric acid and said pyrethrin.

5. The method of claim 1 comprising the step of screening said drying agent to a particle screen size smaller than about 250 mesh prior to mixing said drying agent with said pet food, said boric acid and said pyrethrin.

6. The method of claim 5 comprising the step of comminuting said pet food to a particle screen size between about 100 mesh and about 400 mesh prior to mixing said pet food with said boric acid and said pyrethrin.

7. The method of claim 6 comprising the step of screening said boric acid to a particle screen size smaller than about 250 mesh prior to mixing said boric acid with said pet food, said pyrethrin and said drying agent.

8. A method of preparing an insecticidal bait composition comprising a comminuted, flowable mixture of dry pet food comprising by weight at least from about 8% to about 12% fat, a colloidal drying agent for coating and absorbing moisture from said pet food, powdered boric acid present in said composition in a weight percent of from about 10% to about 18% and a synthetic pyrethrin present in said composition in a weight percent of from about 0.25% to about 0.55%, comprising the steps of reducing substantially dry, commercially available pet food to a particle screen size of between about 100 mesh and about 400 mesh; adding commercial-grade boric acid having a particle size smaller than about 250 mesh to the pet food; blending a powdered, synthetic pyrethroid with the pet food and boric acid mixture; and screening a clay drying agent to a particle size smaller than about 250 mesh and mixing the clay drying agent with the pet food, boric acid and pyrethroid mixture to form a fine, dry, powdered bait composition effective for killing scavenging insects.

* * * * *